US012797189B2

(12) United States Patent
Heniford

(10) Patent No.: US 12,797,189 B2
(45) Date of Patent: Nov. 17, 2026

(54) HEART VALVE STENT AND PROSTHETIC HEART VALVE STRUCTURE THEREOF

(71) Applicant: Shanqian (Zhuhai) Biomaterials Technology Co., Ltd., Zhuhai (CN)

(72) Inventor: Ryan Heniford, Guangdong (CN)

(73) Assignee: SHANQIAN (ZHUHAI) BIOMATERIALS TECHNOLOGY CO., LTD., Zhuhai (CN)

( * ) Notice: Subject to any disclaimer, the term of this patent is extended or adjusted under 35 U.S.C. 154(b) by 713 days.

(21) Appl. No.: 18/256,437

(22) PCT Filed: Jan. 7, 2021

(86) PCT No.: PCT/CN2021/135962
§ 371 (c)(1),
(2) Date: Jun. 8, 2023

(87) PCT Pub. No.: WO2022/121872
PCT Pub. Date: Jun. 16, 2022

(65) Prior Publication Data
US 2024/0024100 A1 Jan. 25, 2024

(30) Foreign Application Priority Data
Dec. 11, 2020 (CN) ......................... 202011463945.9

(51) Int. Cl.
*A61F 2/24* (2006.01)

(52) U.S. Cl.
CPC .......... *A61F 2/2418* (2013.01); *A61F 2/2412* (2013.01); *A61F 2210/0057* (2013.01);
(Continued)

(58) Field of Classification Search
CPC ............ A61F 2/24-2424; A61F 2/2475; A61F 2250/0018; A61F 2250/0029
See application file for complete search history.

(56) References Cited

U.S. PATENT DOCUMENTS 6,454,799 B1 9/2002 Schreck
10,039,640 B2 8/2018 Grundeman et al.
(Continued)

FOREIGN PATENT DOCUMENTS

AU 2015268755 A1 6/2017
CN 105263445 A 1/2016
(Continued)

OTHER PUBLICATIONS

International Search Report and Written Opinion issued Mar. 1, 2022, in PCT/CN2021/135962, 21 pages.
(Continued)

*Primary Examiner* — Rebecca S Preston
(74) *Attorney, Agent, or Firm* — Vorys, Sater, Seymour and Pease LLP; Rex W. Miller, II

(57) ABSTRACT

A heart valve stent and a prosthetic heart valve structure thereof. Wherein, the heart valve stent comprises a stent body (1); a joint member (2) comprising a fixed part and an elastic stretching part connected to the fixed part, an end of the elastic stretching part away from the fixed part is a movable end. By means of optimal design of the stent structure, the service life of a prosthetic heart valve mounted on the stent is prolonged, and meanwhile, a material with lower elasticity can be used to achieve a valve performance comparable to that achieved by a material with higher elasticity in the prior art; moreover, a leaflet assembly (31) is enabled to close more quickly with less external force, which has significant effects.

7 Claims, 3 Drawing Sheets

(52) U.S. Cl.
CPC ................. *A61F 2220/0075* (2013.01); *A61F 2220/0091* (2013.01); *A61F 2230/0019* (2013.01); *A61F 2250/0018* (2013.01); *A61F 2250/0029* (2013.01)

(56) References Cited

U.S. PATENT DOCUMENTS

| | | | | |
|---|---|---|---|---|
| 10,433,958 | B2 | 10/2019 | Levi et al. | |
| 10,441,415 | B2 | 10/2019 | Johnson et al. | |
| 10,524,902 | B2 | 1/2020 | Gründeman et al. | |
| 2004/0186565 | A1* | 9/2004 | Schreck | A61F 2/2427 623/2.38 |
| 2012/0078357 | A1 | 3/2012 | Conklin | |
| 2014/0228945 | A1* | 8/2014 | Valdez | A61F 2/2412 623/2.18 |
| 2018/0289475 | A1* | 10/2018 | Chung | A61F 2/2409 |
| 2023/0063894 | A1 | 3/2023 | Nemoto et al. | |
| 2023/0181316 | A1 | 6/2023 | Cao et al. | |

FOREIGN PATENT DOCUMENTS

| | | | |
|---|---|---|---|
| CN | 110090094 | A | 8/2019 |
| CN | 111281605 | A | 6/2020 |
| CN | 212089843 | U | 12/2020 |
| CN | 214908660 | U | 11/2021 |
| JP | 2013543399 | A | 12/2013 |
| JP | 2013543406 | A | 12/2013 |
| WO | 2017122795 | A1 | 7/2017 |

OTHER PUBLICATIONS

First Office Action issued Feb. 14, 2024, in Japanese Patent Application No. 2023-535526, 10 pages.

Extended European Search Report issued Apr. 4, 2024, in European Patent Application No. 21902577.2, 7 pages.

Second Office Action issued Jun. 18, 2024, in Japanese Patent Application No. 2023-535526, 10 pages.

* cited by examiner

HEART VALVE STENT AND PROSTHETIC HEART VALVE STRUCTURE THEREOF

CROSS-REFERENCE TO RELATED APPLICATIONS

This application is a national stage of International Patent Application PCT/CN2021/135962 filed Dec. 7, 2021, which claims priority to Chinese Patent Application No. 202011463945.9 filed Dec. 11, 2020, which are incorporated by reference herein in their entirety.

TECHNICAL FIELD

The present application relates to the field of medical devices, in particular relates to a heart valve stent and a prosthetic heart valve structure thereof.

BACKGROUND

Most prosthetic heart valve stents delivered through catheters only comprise metal components, such metal components are cut from thin-walled pipes by laser or are made from fine metal wires, the metal components are then adapted to construct the desired shape. A prosthetic heart valve structure is obtained by fixing a heart valve to a prosthetic heart valve stent and assembling them together. By the above-mentioned way of assembling the stent and the heart valve together, the heart valve can also be delivered through a small catheter with an inner diameter as low as 14 Fr, thus effectively implementing Transcatheter Aortic Valve Replacement (TAVR).

In the assembly of prosthetic heart valve structures, because tissue of animal origin has elasticity similar to that of native valve tissue, such tissue of animal origin is often used as a substitute material for valve leaflets to form a tissue heart valve. However, tissue of animal origin, which is often regarded as a "natural" material, has a limitation in its long-term durability, such a limitation is well documented in academic literature, clinical practice, and datasets. Therefore, Transcatheter Aortic Valve Replacement (TAVR) using a heart valve made of tissue of animal origin is generally not recommended for patients under 60 years of age.

To overcome the limitations of long-term durability, one solution is to use synthetic materials known to have high durability and biocompatibility instead of leaflet materials. However, when compared to alternative materials based on tissue of animal origin, although the synthetic materials are ideal materials due to their high strength and fatigue life, most synthetic materials have low elasticity, which limits their use in heart valve leaflet applications. In particular, most leaflet designs considered in the prior art are aimed to replicate the anatomical shape and function of native valves, as a leaflet assembly has two states of an open state and a closed state, and the heart valve stent is harder than leaflet materials, therefore, when the leaflet assembly is in a closed state, the leaflet junction of connection between the leaflet assembly and the heart valve stent will generate a certain amount of cyclic load, which would adversely affect its service life.

For example, U.S. patent U.S. Ser. No. 10/524,902 B2 discloses a heart valve made of a leaflet material with significantly less elasticity than native tissue. The specific assembly method between the leaflet assembly and the heart valve stent is as follows: the leaflet assembly comprises several leaflets and a suture ring that are integrally formed, a leaflet junction is located between every two adjacent leaflets in the leaflet assembly, and the leaflet junction is directly fixed to the suture ring and thereby fixed to the heart valve stent via the suture ring. The above-mentioned structure only simulates and replicates the anatomical shape and function of a native valve. In this case, each design described in the literature U.S. Ser. No. 10/524,902 B2 has stress concentration at the location where the leaflet junction is fixed to the suture ring, which greatly limits the service life of the valve.

SUMMARY

Therefore, the technical problem to be solved by the present application is to overcome the defect that the structural design in the prior art greatly limits the service life of the valve, so as to provide a stent and a prosthetic heart valve structure thereof that effectively reduce the stress concentration at the location where the leaflet junction is fixed to the suture ring, and thus prolong the service life thereof.

A heart valve stent is provided and comprises:

a stent body;

a joint member comprising a fixed part and an elastic stretching part connected to the fixed part, wherein an end of the elastic stretching part away from the fixed part is a movable end.

The joint member has a long strip shape.

When the elastic joint member is in an original state, a central axis of the joint member is parallel to a central axis of the stent body.

The elastic stretching part is connected to a leaflet junction, wherein the leaflet junction is a connection junction between every two adjacent leaflets in a heart valve prosthesis.

The length of the elastic stretching part is the same as the length of the leaflet junction; and/or the number of the joint member is the same as the number of the leaflet junction, wherein one joint member is fixed at each leaflet junction.

The joint member is formed by an elastic material with biocompatibility.

The fixed part is integrally formed with the elastic stretching part.

The elastic stretching part extends beyond the stent body in an axial direction of the stent body.

Cross-section of the elastic stretching part has a rectangular shape.

A prosthetic heart valve structure is provided and comprises:

- a heart valve stent as mentioned above,
- a heart valve prosthesis comprising a leaflet assembly and a suture ring that fixes the leaflet assembly together, wherein the elastic stretching part is connected to a leaflet junction of the heart valve prosthesis which is a connection junction between every two adjacent leaflets of the leaflet assembly.

A prosthetic heart valve structure is provided and comprises:

- a stent body;
- a heart valve prosthesis comprising a leaflet assembly and a suture ring that fixes leaflet assembly together, wherein a connection junction between every two adjacent leaflets of the leaflet assembly forms a leaflet junction of the heart valve prosthesis;
- a joint member comprising a fixed part and an elastic stretching part connected to the fixed part, wherein the fixed part is connected to the suture ring, and the elastic stretching part is connected to the leaflet junction.

The heart valve prosthesis is a woven fabric, and the joint member is arranged inside the woven fabric.

The fixed part of the joint member is located between the stent body and the suture ring.

The joint member has a long strip shape, and a central axis of the joint member is parallel to a central axis of the stent body; the length of the elastic stretching part is the same as the length of the leaflet junction.

The number of the joint member is the same as the number of the leaflet junction, wherein one joint member is fixed at each leaflet junction.

The joint member is formed by an elastic material with biocompatibility.

The technical solution of the present application has the following advantages:

1. In the heart valve stent provided by the present application, a joint member is arranged, a fixed part of which is fixed on the stent body, and one end of an elastic stretching part is connected to the fixed part, while the other end of the elastic stretching part away from the fixed part is a movable end which is used to connect with a leaflet junction of the heart valve prosthesis. By the arrangement of the above-mentioned structure, it is possible to provide a certain movement margin for the leaflet junction of the heart valve prosthesis connected to the stent body when using the stent of the present application, thereby reducing the stress concentration at the location where the leaflet junction is fixed to a suture ring on the stent body, dispersing the stress from the fixing location onto the entire joint member, and thus greatly prolonging the service life of the heart valve prosthesis mounted on the heart valve stent;

Meanwhile, the structure of the present application can also cause the elastic stretching part between the leaflet junction and the joint member to tilt towards the center of the valve, which not only reduces stress and prolongs the service life, but also make it possible to use a material with lower elasticity to produce the leaflet assembly to achieve a valve performance comparable to that achieved by using a material with higher elasticity to produce the leaflet assembly in the prior art; meanwhile, the leaflet assembly is also enabled to close more quickly with less external force, which has significant effects.

2. The present application also provides a prosthetic heart valve structure, which comprises an improved heart valve stent according to the present application and can achieve the same effects as the above-mentioned heart valve stent.

3. The present application provides another prosthetic heart valve structure. Specifically, the joint member is directly woven or sutured at the leaflet junction of the leaflet assembly in the weaving process of the heart valve prosthesis. When fixed on the stent body of an existing structure, it can not only achieve the above-mentioned effects of the heart valve stent of the present application, but also effectively increase the thickness of the leaflet junction, thereby better facilitating the positioning of the heart valve prosthesis on the stent body, facilitating subsequent assembly work, reducing assembly time, and improving assembly efficiency.

BRIEF DESCRIPTION OF THE DRAWINGS

In order to more clearly explain the technical solutions in the specific embodiments of the present application or in the prior art, the drawings needed for describing the specific embodiments or the prior art will be briefly introduced hereinafter. Apparently, the drawings described below are just some embodiments of the present application, and for a person with ordinary skill in the art, other drawings can also be obtained based on these drawings without expenditure of any creative labor.

REFERENCE NUMERALS

Figure 1:
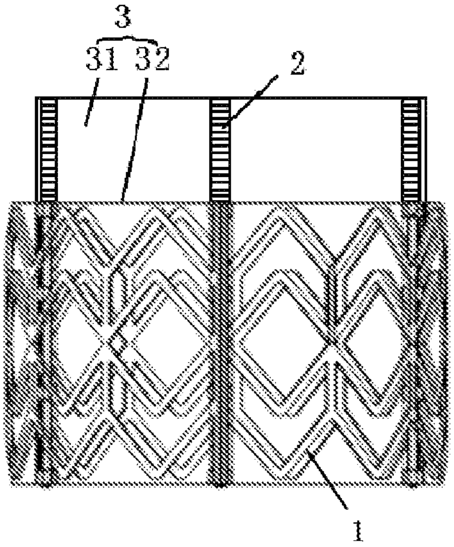
FIG. 1 is a structural schematic diagram of the heart valve prosthesis in the open state after being mounted on a stent in the present application.

1. Stent body; 2. Joint member; 3. Heart valve prosthesis; 31. Leaflet assembly; 32. Suture ring.

DETAILED DESCRIPTION

The technical solution of the present application will be described clearly and completely hereinafter in combination with the drawings. Apparently, the described embodiments are part of the embodiments of the present application, not all of them. Based on the embodiments described in the present application, all other embodiments, obtainable by a person with ordinary skill in the art without expenditure of any creative labor, belong to the protection scope of the present application.

In the description of the present application, it should be noted that the orientation or positional relationship indicated by the terms "center", "top", "bottom", "left", "right", "vertical", "horizontal", "inside", "outside", etc. are based on the orientation or positional relationship shown in the drawings, which are only used for the convenience of describing the present application and simplifying the description, rather than indicating or implying that the device or element referred to must have a specific orientation or be constructed and operated in a specific orientation, and therefore should not be understood as a limitation to the present application. In addition, the terms "first", "second" and "third" are only used for descriptive purposes and should not be understood as indicating or implying relative importance.

In the description of the present application, it should be noted that, unless otherwise clearly specified and defined, the terms "mounted", "connected" and "coupled" should be understood in a broad sense, for example, it can be fixed connection, detachable connection or integral connection; it can be direct connection, or indirect connection through an intermediate medium. For a person with ordinary skill in the art, the specific meanings of the above-mentioned terms in the present application can be understood according to specific circumstances.

In addition, the technical features involved in different embodiments of the present application described below can be combined with each other as long as they do not conflict with each other.

Embodiment 1

Figure 2:
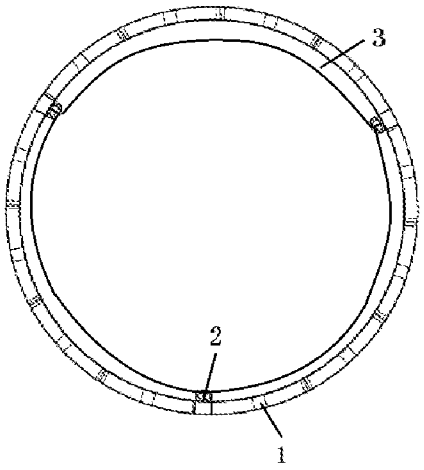
FIG. 2 is a top view of the structure shown in FIG. 1.

A heart valve stent, as shown in FIGS. 1 and 2, comprises a stent body 1 and a joint member 2. Wherein, the joint member 2 comprises a fixed part and an elastic stretching part; the elastic stretching part is connected to the fixed part 1 through the fixed part; an end of the elastic stretching part away from the fixed part is a movable end; the movable end is used for connecting with a leaflet junction of a heart valve prosthesis 3. When in use, the elastic stretching part has an original state and a stretching state, wherein the movable end is tilted and shifted towards the center of the stent body in the stretching state.

Figure 3:
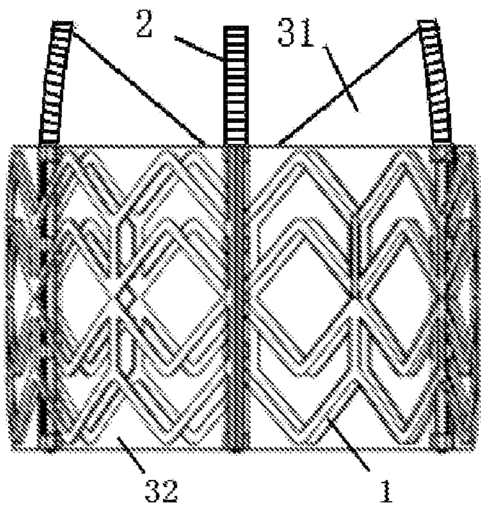
FIG. 3 is a structural schematic diagram of the heart valve prosthesis in the closed state after being mounted on a stent in the present application.
Figure 4:
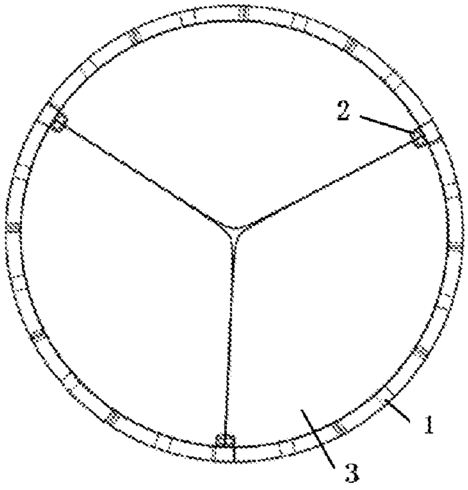
FIG. 4 is a top view of the structure shown in FIG. 3.

In the present embodiment, a joint member 2 is added. The fixed part of the joint member is fixed on the stent body, and one end of the elastic stretching part thereof is connected to the fixed part, while the other end of the elastic stretching part away from the fixed part is a movable end, which is used for connecting with a leaflet junction of the heart valve prosthesis. By the arrangement of the above-mentioned structure, it is possible to provide a certain movement margin for the leaflet junction of the heart valve prosthesis connected to the stent body when using the stent of the present embodiment, thereby reducing the stress concentration at the location where the leaflet junction is fixed to a suture ring on the stent body, dispersing the stress from the fixing location onto the entire joint member, and thus greatly prolonging the service life of the heart valve prosthesis mounted on the heart valve stent;

Meanwhile, by using the structure of the present embodiment, for a heart valve prosthesis 3 formed by a leaflet material with a fracture elongation of less than 20%, 10%, or 5%, when the leaflet assembly is closed, since the anchor point at the connection between the stent and the leaflet junction on the leaflet assembly is the joint member which has elasticity, the elastic stretching part of the joint member between the leaflet junction and the joint member 2 can be tilted towards the center of the valve, as shown in FIGS. 3 and 4, which can not only reduce stress and prolong the service life, but also make it possible to use a material with lower elasticity to achieve a valve performance comparable to that achieved by using a material with higher elasticity in the prior art; meanwhile, the leaflet assembly is also enabled to close more quickly with less external force, which has significant effects.

In the present embodiment, the fixed part may be a circular structure similar to the stent body or may be a structure of other shapes, as long as it is a structure that can be fixedly connected to the stent body 1. The elastic stretching part is used for connecting to the leaflet junction, and the connection manner includes, but is not limited to, sewing, bonding, welding, or mechanical connection. In the present embodiment, the elastic stretching part is provided as a long strip structure, arranged along a connection seam between every two adjacent leaflets, that is, the elastic stretching part is fixed at the leaflet junction, and the number of elastic stretching parts is the same as the number of leaflets in the leaflet assembly. The number of leaflets in an ordinary leaflet assembly is two or three, and the number of elastic stretching parts is correspondingly set to two or three.

As one of the setting manners, in the present embodiment, the joint member 2 is overall arranged in a long strip shape, that is, the fixed part and the elastic stretching part are integrally formed. One end of the joint member 2 is a fixed part for fixedly connecting to the stent body 1, the other end of the joint member 2 is an elastic stretching part with a movable end, and the movable end is used for connection with the leaflet junction. Taking the case of the structure applied to an aorta as an example, the heart valve prosthesis 3 is a tricuspid valve, and the number of leaflets is three, so the number of joint members 2 on the stent body 1 in the present embodiment is also set to three. One joint member 2 is fixed at each of the leaflet junctions. The movable end of the elastic stretching part may be lower than the position of the top of the stent body 1 in the axial direction of the stent body 1, or may extend beyond the stent body 1. In the present embodiment, as shown in FIGS. 1 to 4, the elastic stretching part is set to extend beyond the stent body in the axial direction of the stent body, and meanwhile the length of the elastic stretching part can also be set to be the same as the length of the leaflet junction.

In the present embodiment, the heart valve prosthesis 3 may be fixed to the joint member 2 from an inner side of the stent body 1, and the heart valve prosthesis 3 may also be fixed to the joint member 2 2 from an outer side of the stent body 1. In the present embodiment, the manner of fixing from an inner side is used to minimize the contour of the prosthetic heart valve structure when being delivered through a catheter and reduce the wall thickness of the instrument. In the present embodiment, a portion of the joint member 2 may be exposed to the bloodstream, and meanwhile another portion of the joint member 2 may also be wrapped inside the heart valve prosthesis 3. When wrapping is adopted for processing, the elastic stretching part can be wrapped in the leaflet junction of the heart valve prosthesis 3 by suturing. Although this manner increases the contour of the structure during transcatheter delivery, it can further reduce the potential risk of tissue rejection and achieve better results.

In the present embodiment, the joint member 2 is preferably formed by an elastic material with biocompatibility, such as thermoplastic polyurethane rubber. The joint member 2 is formed by extrusion or injection molding, and the material optimization can effectively reduce tissue rejection caused by surface exposure, such as collagen formation and thickening of the leaflet layer.

A section of the elastic stretching part perpendicular to the central axis thereof is the cross-section thereof. Under the premise of maintaining optimal valve dynamics, the shape of the cross-section of the elastic stretching part may also vary, depending on the shape of the stent used and the connection manner between the leaflet of the heart valve prosthesis and the heart valve stent. The cross-section of the elastic stretching part may be circular, square, polygonal, irregular, etc. In the present embodiment, the cross-section of the elastic stretching part is set to have a rectangular shape and the elastic stretching part is connected to the leaflet junction in the heart valve prosthesis by bonding, which can effectively meet the requirement of minimum valve contour during delivery.

Embodiment 2

A prosthetic heart valve structure comprises a heart valve stent according to Embodiment 1 and a heart valve prosthesis 3; wherein the heart valve prosthesis 3 comprises a leaflet assembly 31 and a suture ring 32 that fixes the leaflet assembly 31 together, a connection junction between every two adjacent leaflets of the leaflet assembly 31 forms a leaflet junction of the heart valve prosthesis 3.

The connection manner between the heart valve prosthesis 3 and the heart valve stent is as follows: connecting the elastic stretching part of the heart valve stent to the leaflet junction of the heart valve prosthesis 3, and meanwhile fixing the suture ring 32 of the heart valve prosthesis 3 to the stent body 1 of the heart valve stent. The connection manner between the above-mentioned elastic stretching part and the leaflet junction, as well as the fixation manner between the above-mentioned suture ring 32 and the stent body 1, comprise but are not limited to sewing, bonding, welding, or mechanical connection.

Embodiment 3

A prosthetic heart valve structure comprises a stent body 1, a heart valve prosthesis 3, and a joint member 2. Wherein, the heart valve prosthesis 3 comprises a leaflet assembly 31 and a suture ring 32 that fixes the leaflet assembly 31 together; the joint member 2 comprises a fixed part and an elastic stretching part. A connection junction between every two adjacent leaflets of the leaflet assembly 31 forms a leaflet junction of the heart valve prosthesis 3. The fixed part of the joint member 2 is connected to the suture ring 32, and the elastic stretching part of the joint member 2 is connected to the leaflet junction.

In the present embodiment, the fixed part of the joint member 2 may be located between the stent body 1 and the suture ring 32, or the suture ring 32 may also be arranged between the fixed part of the joint member 2 and the stent body 1; then it only requires to connect the elastic stretching part to the leaflet junction of the heart valve prosthesis 3.

Specifically, when the manner wherein the fixed part is located between the stent body 1 and the suture ring 32 is adopted, only the entire joint member 2 is exposed to the outside of the heart valve prosthesis 3, that is, the joint member 2 may be fixed on the peripheral surface of the heart valve prosthesis 3. It is only necessary to ensure that the fixed part is fixedly connected to the suture ring 32 and the elastic stretching part is fixedly connected to the leaflet junction. At this time, when the heart valve prosthesis 3 is fixedly connected to the stent body 1, the fixation of the joint member 2 on the stent body 1 can be effectively achieved; meanwhile, the elastic stretching part may also be embedded into the woven fabric forming the heart valve prosthesis 3, that is, the elastic stretching part may be woven or sutured to the leaflet junction of the heart valve prosthesis 3. At this time, the joint member 2 in the present embodiment may be formed by an elastic material with biocompatibility, which effectively reduces tissue rejection inside the valve caused by foreign objects.

When the manner wherein the suture ring 32 is located between the fixed part and the stent body 1 is adopted, the structure of the joint member 2 connected to the stent body 1 through the suture ring 32 is described in detail in the present embodiment. Specifically, the joint member 2 is firstly fixed at the leaflet junction of the heart valve prosthesis 3, and then it is connected to the stent body 1 through the suture ring 32 of the heart valve prosthesis 3. More specifically, in the present embodiment, the heart valve prosthesis 3 is a woven fabric, the joint member 2 is provided to have a long strip shape, and the joint member 2 is sewn and wrapped inside the leaflet junction during the weaving process of the heart valve prosthesis 3; alternatively, the joint member 2 is provided as a single fiber structure, which is woven as a weft thread at the leaflet junction during the weaving process of the heart valve prosthesis 3, the weft thread can be completely sealed into the leaflet junction of the leaflet assembly by using other fibers, thereby reducing tissue rejection related to high carbon materials inside the valve.

Figure 5:
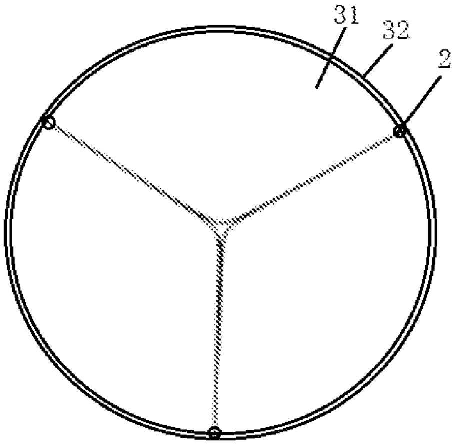
FIG. 5 is a schematic diagram of the structure of the joint member wrapped in the leaflet junction of the heart valve prosthesis in the present application.

At this time, as shown in FIG. 5, the leaflet junction of the heart valve prosthesis 3 incorporates the joint member 2, so the thickness of the leaflet junction increases relatively. It is more convenient to assemble the heart valve prosthesis 3 on the stent due to the increase in thickness thereof, which effectively reduces the assembly time. Moreover, the increase in thickness at the leaflet junction can effectively reduce the positioning time for the heart valve prosthesis 3, reduce the trimming and sewing work after assembly, and reduce the subsequent assembly workload, which has more significant effects.

Meanwhile, as shown in FIG. 5, in the present embodiment, the number of the joint member 2 is set to be the same as the number of the leaflet junction, and one joint member 2 is fixed at each leaflet junction. Moreover, a central axis of each joint member 2 is parallel to a central axis of the stent body 1, and the length of the elastic stretching part is the same as the length of the leaflet junction.

Apparently, the above embodiments are only examples for clear illustration, not for limitation of embodiments. For a person with ordinary skill in the art, other changes or modifications in different forms can be made on the basis of the above description. It is unnecessary and impossible to exhaustively enumerate all embodiments herein. Any obvious changes or modifications derived therefrom are still within the protection scope of the present application.

The invention claimed is:

1. A prosthetic heart valve structure, comprising:

a heart valve stent, comprising a stent body (1) and a joint member (2), wherein the joint member (2) comprises a fixed part and an elastic stretching part connected to the fixed part, and an end of the elastic stretching part away from the fixed part is a movable end;

a heart valve prosthesis (3) comprising a leaflet assembly (31) and a suture tube (32) that fixes the leaflet assembly (31) together, wherein the elastic stretching part is connected to a leaflet junction of the heart valve prosthesis (3) which is a connection junction between every two adjacent leaflets of the leaflet assembly (31);

wherein the heart valve prosthesis (3) is a woven fabric, and the joint member (2) is woven as a weft thread at the leaflet junction of the heart valve prosthesis (3).

2. The prosthetic heart valve structure according to claim 1, characterized in that: the fixed part is connected to the suture tube (32).

3. The prosthetic heart valve structure according to claim 1, characterized in that the joint member (2) has a singl fiber structure, and a central axis of the joint member (2) is parallel to a central axis of the stent body (1); a length of the elastic stretching part is the same as a length of the leaflet junction.

4. The prosthetic heart valve structure according to claim 1, characterized in that the number of the joint member (2) is the same as the number of the leaflet junction, wherein one joint member (2) is fixed at each leaflet junction.

5. The prosthetic heart valve structure according to claim 1, characterized in that the joint member (2) is formed by an elastic material with biocompatibility.

6. The heart valve stent according to claim 1, characterized in that the fixed part is integrally formed with the elastic stretching part.

7. The heart valve stent according to claim 1, characterized in that the elastic stretching part extends beyond the stent body (1) in an axial direction of the stent body (1).

* * * * *